United States Patent [19]

Spector

[11] Patent Number: 4,814,212
[45] Date of Patent: Mar. 21, 1989

[54] AUTOMOBILE AIR FRESHENER UNIT

[76] Inventor: Donald Spector, 380 Mountain Rd., Union City, N.J. 07087

[21] Appl. No.: 190,642

[22] Filed: May 5, 1988

[51] Int. Cl.⁴ .............................................. G09F 21/4
[52] U.S. Cl. ........................................ 428/14; 239/57; 428/46; 428/905
[58] Field of Search ................... 40/152; 428/905, 14, 428/45, 46; 239/57

[56] References Cited

U.S. PATENT DOCUMENTS

| | | | |
|---|---|---|---|
| 2,577,320 | 12/1951 | Fenyo | 428/905 X |
| 2,959,882 | 11/1960 | Krull | 40/152 |
| 3,878,632 | 4/1975 | Berggren et al. | 40/152 |
| 4,696,844 | 9/1987 | Spector | 428/905 X |
| 4,714,984 | 12/1987 | Spector | 428/905 X |
| 4,720,409 | 1/1988 | Spector | 428/46 |

Primary Examiner—Henry F. Epstein
Attorney, Agent, or Firm—Michael Ebert

[57] ABSTRACT

A replaceable air freshener unit adapted to be adhered to an automobile window to suffuse the interior of the vehicle with a pleasing or stimulating aroma. The unit is constituted by a bipartite rectangular frame and a transparent film chip having artwork thereon, the film chip being mounted behind the back section of the frame. The rear surface of the chip is coated with a layer of pressure-sensitive adhesive whereby the unit may be attached to the window at an appropriate site. The front section of the frame is impregnated with a volatile fragrance that is thematically related to the artwork and slowly released into the atmosphere. When the fragrance is exhausted, the unit may readily be detached from the window and replaced.

8 Claims, 1 Drawing Sheet

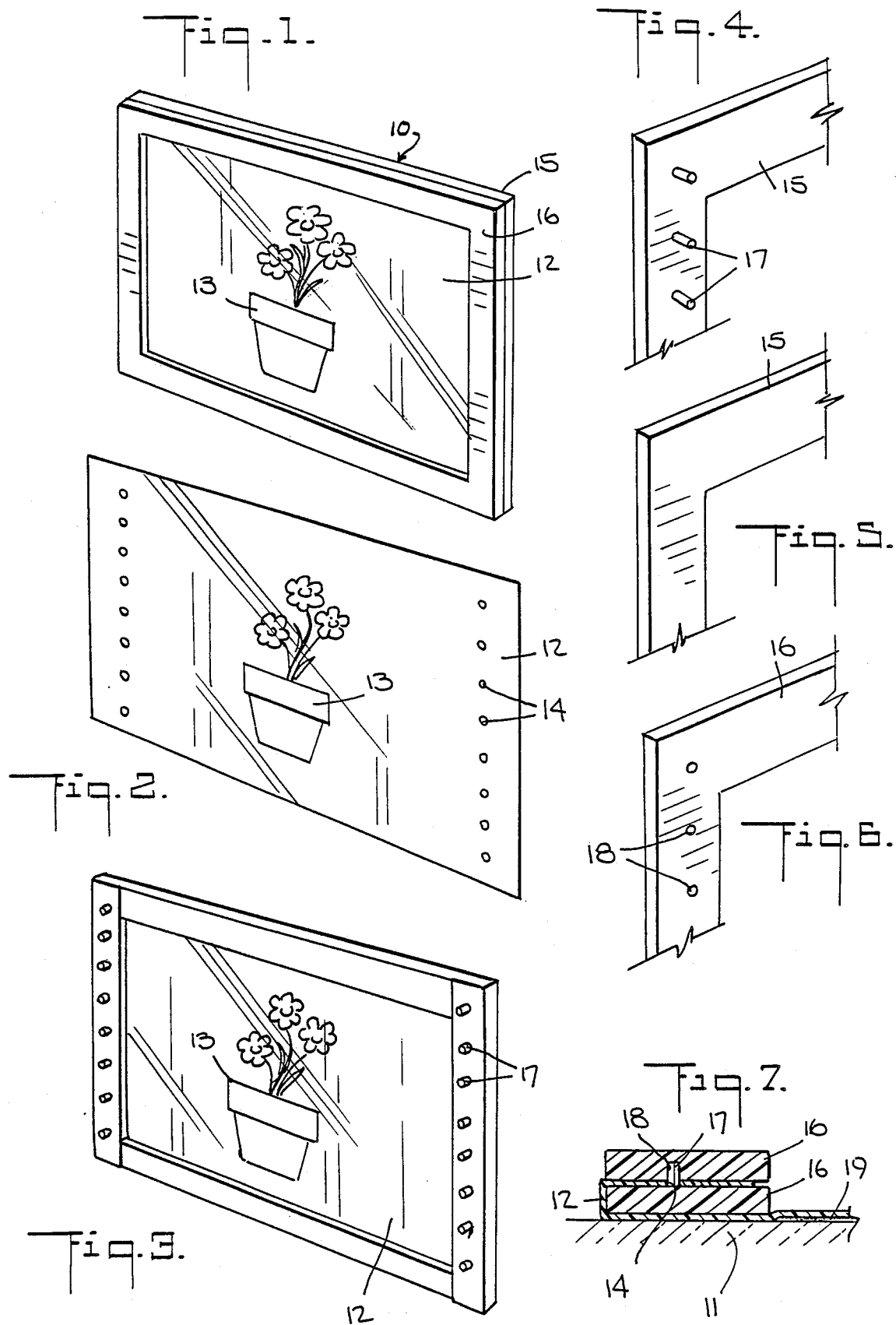

AUTOMOBILE AIR FRESHENER UNIT

BACKGROUND OF INVENTION

1. Field of Invention:

This invention relates generally to air fresheners which release an aroma into the atmosphere, and more particularly to a replaceable air freshener unit that is adherable to an automobile window or other flat substrate in the automobile to render the interior atmosphere thereof more pleasing.

2. Status of Prior Art:

As used herein, the term "aroma" or "fragrance" is not limited to perfume-like odors, but encompasses any odor that is suitable as an air freshener to condition, modify or otherwise charge the ambient atmosphere.

The aroma of perfumes and perfume-based products such as colognes and toilet waters was originally derived from the essential oil of plants. However, since the early 19th century, chemists have succeeded in analyzing many essential oils and in creating thousands of synthetics, some simulating natural products and others yielding altogether new scents. Perfumes today are largely blends of natural and synthetic scents and of fixatives which equalize vaporization and enhance pungency. In most liquid scents, the ingredients are combined with a highly volatile alcohol carrier.

The concern of the present invention is with the atmosphere in the interior of an automobile, and in this context, a fragrance emitted by an air freshener may be such as to render the atmosphere more pleasing to the occupants of the vehicle, or take the form of an aromatic stimulant to discourage the driver from falling asleep at the wheel.

My prior 1988 U.S. Pat. No. 4,720,409 discloses an air freshener of the film laminate type which is adherable to a wall tile in a bathroom or kitchen to render the atmosphere more pleasing. The same laminate, as noted in this patent, can be applied to the window of an automobile.

This film laminate includes a transparent, plastic face film impregnated with a volatile fragrance that is slowly released from the film. The concentration of the fragrance in the film is such as to result in prolonged emission. The face film is laminated to a transparent backing film in a manner which does not impair the transparency of the laminate.

Imprinted on the front surface of the backing film is artwork representing an aroma-producing object of some sort. This artwork is effectively sandwiched between the face film and the backing film and is thereby protected. The rear surface of the backing film is coated with a low tack, pressure-sensitive adhesive. Thus, the laminate may be adhered onto a smooth tile or window and later pulled therefrom when the fragrance is exhausted.

This laminate is a highly effective air freshener when applied to a bathroom or kitchen tile. But when the laminate is applied to a window of an automobile, a serious problem arises; for then the laminate is exposed to sunlight and may be subjected to a tremendous buildup of heat. In certain seasons, when a car whose windows are closed is exposed to sunlight, the interior temperature may rise well above 110° F.

As noted in my prior patent, the fragrance-emitting face film is preferably made of bi-axially oriented polymeric material such as EVA (ethylene vinyl acetate), whereas the backing film is made of polyester (Mylar) which is laminated to the face film by heat and pressure or other means which will not impair the transparency of the laminate.

Bur if this laminate is subjected in an automobile to elevated temperatures, the EVA face film, because of its temperature coefficient of expansion, will then expand to a greater degree than the Mylar backing film, resulting in delamination of the laminate. Moreover, because the fragrance is impregnated throughout the entire area of the face film, when this relatively broad area is subjected to an elevated temperature, the result is an excessively rapid emission of the fragrance. An automobile interior is a confined space; and when the windows are closed, it takes a relatively small amount of aromatic vapor to charge the interior atmosphere. But if the amount of aromatic vapor exuded into this interior is excessive, the fragrance will then be too "heavy," and to this extent may be displeasing to the occupants of the vehicle.

SUMMARY OF INVENTION

In view of the foregoing, the main object of this invention is to provide a replaceable air freshener unit which is adherable to a window in an automobile or other flat substrate and which functions to suffuse the interior atmosphere of the automobile with a pleasing or stimulating aroma.

More particularly, an object of this invention is to provide a unit of the above type capable of withstanding the elevated temperatures which often prevail in automobile interiors.

Also an object of the invention is to provide a low cost unit of the above type which when its fragrance is exhausted is readily replaceable.

A significant feature of the invention is that the air freshener unit not only functions as an aroma generator, but it also provides a framed miniature artwork whose subject matter has a characteristic aroma, such as a flower, or a woodburning fireplace, the aroma exuded by the unit being thematically related to the artwork.

Briefly stated, these objects are attained in a replaceable air freshener unit adapted to be adhered to an automobile window to suffuse the interior of the vehicle with a pleasing or stimulating aroma. The unit is constituted by a bipartite rectangular frame and transparent film chip having artwork thereon, the film chip being mounted behind the back section of the frame. The rear surface of the chip is coated with a layer of pressure-sensitive adhesive whereby the unit may be attached to the window at an appropriate site. The front section of the frame is impregnated with a volatile fragrance that is thematically related to the artwork and slowly released into the atmosphere. When the fragrance is exhausted, the unit may readily be detached from the window and replaced.

BRIEF DESCRIPTION OF DRAWINGS

For a better understanding of the invention as well as other objects and further features thereof, reference is made to the following detailed description to be read in conjunction with the accompanying drawings, wherein:

FIG. 1 is a perspective view of an air freshener unit in accordance with the invention adhered to an automobile window;

FIG. 2 is a separate view of the film chip included in the unit;

FIG. 3 shows the film chip when mounted behind the back section of a bipartite frame included in the unit;

FIG. 4 shows a corner of the back section of the frame, as seen from its front side;

FIG. 5 shows a corner of the back section of the frame as seen from its rear side;

FIG. 6 shows a corner of the front section of the frame as seen from its rear side; and FIG. 7 is a section taken in the plane indicated by line 7—7 in FIG. 1.

DESCRIPTION OF INVENTION

Referring now to FIG. 1, there is shown an air freshener unit, generally designated by numeral 10, which is adhered to the inner surface of an automobile window 11. The unit functions to slowly release a fragrance into the atmosphere to suffuse the interior of the vehicle with a pleasing or stimulating aroma.

Unit 10 includes a transparent film chip 12 made of a polyester, such as Mylar, having screened or otherwise imprinted thereon an artwork, which in the example illustrated is a flower pot 13. The subject matter of the artwork, is such that it is odoriferous in some way. Thus, in the case of a flower pot containing violets, the aroma would be that of this flower. And should the artwork be that of an orange or other fruit, then the related fragrance is that of the fruit illustrated. The artwork need not be that of a flower, a fruit or a vegetable, for it may show a sea scape, so that the related aroma is then that of a seabreeze. Or it may be an Xmas tree having a pine needle odor.

Chip 12 is provided at either end margin with a row of sprocket holes 14, making it possible to mount the chip behind the back section 15 of a bipartite rectangular frame having a front section 16 provided with complementary rows of sprocket pins 17. The use of conventional bonding agents for this purpose is avoided because of the possibility of delamination when the unit is subjected to elevated temperatures.

This attachment is shown in FIGS. 3 and 4, where it will be seen that the end branches of back section 15 of the frame are provided with a row of sprocket pins 17, film chip 12 being mounted behind back section 15 by folding over the margins of the chip and fitting sprocket holes 14 onto sprocket pins 17.

Back section 15 of the frame is preferably molded of synthetic plastic material such as polyvinyl chloride, the spocket pins 17 being integral with the back section. Front section 16 of the frame is formed of cardboard, open-cell foam plastic or other relatively porous material which is impregnated with a volatile fragrance in a relatively high concentration, preferably 20 to 30%. The nature of the fragrance is such that it is thematically related to the artwork; hence one who views the artwork on the air freshener unit, as the same time effectively smells the artwork. Consequently, the occupant of the vehicle receives a visual impression which is enhanced by a thematically-related olfactory sensation.

The exposed side of the front section 16 of the frame is clean and flat, as shown in FIG. 5, so that film chip 12 appears to be neatly mounted on the frame. The underside of front section 16 is provided with a row of complementary sockets 18 to receive and retain sprocket pins 17 on the back section of the frame. Thus, when the unit is assembled, the folded-over margins of film chip 12, as shown in FIG. 7, are then sandwiched between the corresponding end branches of the front and back frame sections 15 and 16.

Because front section 16 of the frame which is fragrance emissive is isolated from the window by back section 15 of the frame, the front section is somewhat insulated from sunlight impinging on the window. But sunlight serves to illuminate the artwork on the chip which, in practice, may take the form of a photographic transparency. And because the fragrance-emitting area of the front section of the frame is relatively small, even when the interior temperature of the vehicle is high, this temperature will not result in an excessively rapid release of the fragrance.

While there has been shown and described a preferred embodiment of an automobile air freshener unit in accordance with the invention, it will be appreciated that many changes and modifications may be made therein without, however, departing from the essential spirit thereof. Thus, instead of using a pressure-sensitive adhesive layer of the rear surface of the film chip, the film may be of the type having electrostatic properties such that when pressed against the planar surface of a window it will adhere thereto. And instead of securing the film chip to the frame by the sprocket pin arrangement disclosed therein, the film and the frame therefor may be joined by heat and pressure, in which case the film will be of thermoplastic material.

I claim:

1. A replaceable air freshener unit adapted to be adhered onto an automobile window to suffuse the interior of the vehicle with a pleasing or stimulating fragrance and to present a viewer with an illuminated art work, said unit comprising:

A a rectangular frame having an exposed, emissive front section all of whose branches are formed of porous material impregnated with a volatile fragrance that is slowly released into the atmosphere; and B a transparent film chip mounted behind the frame and having a clear, pressure-sensitive adhesive layer on its rear surface, whereby the unit may be adhered to the window at any desired site and thereafter removed therefrom, the chip having artwork thereon which is thematically related to said fragrance, said chip being illuminated by light going through the window.

2. A unit as set forth in claim 1, wherein said frame has a non-emissive rear section.

3. A unit as set forth in claim 2, wherein said chip has end margins provided with sprocket holes, which margins are folded over the rear frame section whose end branches are provided with sprocket pins to receive the sprocket holes and retain the margins.

4. A unit as set forth in claim 3, wherein the end branches of said front section of the frame are provided with sockets to receive and retain the sprocket pins whereby the margins of the chip are sandwiched between corresponding end branches of the front and back frame sections.

5. A unit as set forth in claim 4, wherein said front section is made of cardboard.

6. A unit as set forth in claim 4, wherein said back section is made of synthetic plastic material.

7. A unit as set forth in claim 1, wherein said film is made of polyester.

8. A replaceable air freshener unit adapted to be adhered onto an automobile window to suffuse the interior of the vehicle with a pleasing or stimulating fragrance and to present a viewer with an illuminated art work, said unit comprising:

A a rectangular frame assembly having an exposed, emissive front section all of whose branches are formed of porous material impregnated with a volatile fragrance that is slowly released into the atmosphere; and B a transparent film chip mounted behind the frame, the rear surface of the chip having properties that render it adherable to the window at any desired site whereby the unit may be mounted on the window and thereafter removed therefrom, the chip having artwork thereon which is thematically related to said fragrance, said chip being illuminated by light going through the window.

* * * * *